(12) United States Patent
Moore et al.

(10) Patent No.: US 8,697,133 B2
(45) Date of Patent: Apr. 15, 2014

(54) SLOW RELEASE COMPOSITIONS

(75) Inventors: Barry Douglas Moore, Killearn (GB); Johann Partridge, Glasgow (GB); Louise Bradley, Glasgow (GB); Jan Vos, Glasgow (GB)

(73) Assignee: University of Strathclyde, Glasgow (GB)

( * ) Notice: Subject to any disclaimer, the term of this patent is extended or adjusted under 35 U.S.C. 154(b) by 169 days.

(21) Appl. No.: 12/808,314

(22) PCT Filed: Dec. 15, 2008

(86) PCT No.: PCT/GB2008/004122
§ 371 (c)(1),
(2), (4) Date: Sep. 24, 2010

(87) PCT Pub. No.: WO2009/077732
PCT Pub. Date: Jun. 25, 2009

(65) Prior Publication Data
US 2011/0008450 A1  Jan. 13, 2011

(30) Foreign Application Priority Data
Dec. 15, 2007 (GB) .................................. 0724498.1

(51) Int. Cl.
*A61K 9/14* (2006.01)
*A61K 33/06* (2006.01)
*A61K 33/08* (2006.01)
*A61K 33/10* (2006.01)
*A61K 31/7088* (2006.01)
*A61K 31/715* (2006.01)
*A61K 38/00* (2006.01)

(52) U.S. Cl.
CPC . *A61K 9/14* (2013.01); *A61K 33/06* (2013.01); *A61K 33/08* (2013.01); *A61K 31/7088* (2013.01); *A61K 38/00* (2013.01)
USPC ........... 424/490; 424/489; 424/491; 424/493; 424/130.1; 424/134.1; 514/1.1; 514/23; 514/42; 514/43

(58) Field of Classification Search
None
See application file for complete search history.

(56) References Cited

U.S. PATENT DOCUMENTS

| | | | |
|---|---|---|---|
| 5,324,649 A | 6/1994 | Arnold et al. | |
| 5,662,883 A | 9/1997 | Bagchi et al. | |
| 5,807,746 A | 9/1998 | Lin et al. | |
| 5,945,126 A | 8/1999 | Thanoo et al. | |
| 6,380,324 B1 | 4/2002 | McFadden et al. | |
| 6,824,702 B1 | 11/2004 | Ohrem et al. | |
| 6,825,247 B2 | 11/2004 | Ando et al. | |
| 7,014,869 B2 * | 3/2006 | Moore et al. | 424/490 |
| 7,632,799 B2 * | 12/2009 | Bach et al. | 510/441 |
| 2002/0159954 A1 | 10/2002 | Small et al. | |
| 2003/0158115 A1 | 8/2003 | Toback et al. | |
| 2005/0139144 A1 | 6/2005 | Muller et al. | |
| 2006/0120992 A1 | 6/2006 | Moore et al. | |
| 2006/0167147 A1 * | 7/2006 | Asgari | 524/174 |
| 2006/0292224 A1 | 12/2006 | Moore et al. | |
| 2007/0026065 A1 | 2/2007 | Benke et al. | |
| 2007/0196539 A1 | 8/2007 | Yang et al. | |
| 2008/0286369 A1 | 11/2008 | Moore et al. | |
| 2009/0226530 A1 | 9/2009 | Lassner et al. | |
| 2010/0151247 A1 | 6/2010 | Moore et al. | |

FOREIGN PATENT DOCUMENTS

| | | |
|---|---|---|
| DE | 19925184 A1 | 11/2000 |
| EP | 1674094 A1 | 6/2006 |
| JP | 64-24010 A | 1/1989 |
| WO | 9905302 A1 | 2/1999 |
| WO | 0046147 A2 | 8/2000 |
| WO | 0069887 A2 | 11/2000 |
| WO | 0132125 A2 | 5/2001 |
| WO | 0141811 A2 | 6/2001 |
| WO | 2004062560 A2 | 7/2004 |
| WO | 2006010921 A1 | 2/2006 |

OTHER PUBLICATIONS

Sigma Aldrich, "Subtilisin", "Sigma-Aldrich Enzyme Explorer", 2013 (as accessed on Jan. 9, 2013 via www.sigmaaldrich.com/life-science/metabolomics/enzyme-expolorer/analytical-enzymes/subtilisin.html).

Kreiner, M., et al., "Enzyme-Coated Micro-Crystals: A 1-Step Method for High Activity Biocatalyst Preparation", "Chemical Communications", May 25, 2001, pp. 1096-1097, vol. 2001, No. 12.

Kreiner, M., et al, "DNA-Coated Microcrystals", "Chemical Communications", Apr. 20, 2005, pp. 2675-2676, vol. 2005, No. 21.

Budavari, S., et al., "An Encyclopedia of Chemicals, Drugs, and Biologicals", "The Merck Index: Twelfth Edition", Mar. 15, 1996, p. 1318 Publisher: Merck and Company.

Murdan, S., et al., "Vaccine-Coated Microcrystals: Enhanced Thermal Stability of Diphtheria Toxoid", Sep. 15-17, 2003, p. 1 British Pharmaceutical Conference 2003, Harrogate, United Kingdom.

Hurwitz, H., et al., "Bevacizumab plus Irinotecan, Fluorouracil, and Leucovorin for Metastatic Colorectal Cancer", "The New England Journal of Medicine", Jun. 3, 2004, pp. 2335-2342, vol. 350, No. 23.

* cited by examiner

*Primary Examiner* — Lakshmi Channavajjala
(74) *Attorney, Agent, or Firm* — Hultquist, PLLC; David Bradin

(57) ABSTRACT

The present invention relates to the provision of micron or sub-micron sized particles formed from one or more water-soluble crystals comprising a surface coating comprising one or more bioactive molecules wherein the particles are prepared such that in use the release of the bioactive molecule(s) is/are delayed and/or continually released over a period of time. Processes for the preparation of said particles, as well as the particles themselves are described, as well as uses of the particles.

21 Claims, No Drawings

SEQUENCE LISTING

<160> NUMBER OF SEQ ID NOS: 1

<210> SEQ ID NO 1
<211> LENGTH: 21
<212> TYPE: DNA
<213> ORGANISM: Artificial
<220> FEATURE:
<223> OTHER INFORMATION: Immunostimulatory oligodeoxynucleotides

<400> SEQUENCE: 1
tccatgacgt tcctgaataa t                                          21

SLOW RELEASE COMPOSITIONS

FIELD OF THE INVENTION

The present invention relates to the provision of micron or sub-micron sized particles formed from one or more water-soluble crystals comprising a surface coating comprising one or more bioactive molecules wherein the particles are prepared such that in use the release of the bioactive molecule(s) is/are delayed and/or continually released over a period of time. Processes for the preparation of said particles, as well as the particles themselves are described, as well as uses of the particles.

BACKGROUND OF THE INVENTION

WO 0069887, WO 04/062560 and WO 06/010921, which are incorporated herein by reference, are previous applications filed by some of the present inventors and describe methods of preparing bioactive molecule coated microcrystals.

For certain applications, such as in the field of drug or vaccine delivery to humans and/or animals, it may be desirable in some instances to provide compositions which, when administered, display a slowed and/or delayed release of the bioactive material. Although such a desired feature has been proposed in the prior art, particles so produced do not always display all of the most desirable properties. For example, in terms of protein coated particles, it is generally desirable to be able to accurately control particle size, maintain protein stability upon storage and display an appropriate release profile for an envisaged use. It may also be desirable to use only non-polymeric materials that are natural or biocompatible and to avoid any chemical or structural modifications to the bioactive material. Additionally it would be desirable to avoid coacervation or emulsification techniques for introducing biomolecules into sustained release particles because the solvents and surfactants used can cause denaturation.

It is an object of the present invention to obviate and/or mitigate at least one of the aforementioned disadvantages.

SUMMARY OF THE INVENTION

According to a first aspect there is provided a method of preparing bioactive molecule coated microcrystal which display a delayed and/or prolonged release profile of said bioactive molecule in water and/or aqueous solution, comprising the step of:

carrying out a double decomposition reaction in an organic solvent, between a water soluble inorganic salt present in a water soluble precipitate comprising said bioactive molecule and material capable of forming said microcrystals, and a metal salt dissolved in said organic solvent, whereby said bioactive molecule coated microcrystals are formed comprising a coating of a metal salt, formed by said double decomposition, on the surface of the microcrystals.

It is understood that the metal salt coating the surface of the microcrystals serves to delay and/or prolong the release of said bioactive molecule into water and/or an aqueous solution.

The above method is desirably carried out by a continuous process, where a first aqueous stream comprising said water soluble precipitate is mixed with a second stream comprising a miscible organic solvent. Said organic solvent may comprise said metal salt or this may be provided by way of a third stream.

According to a further aspect, there is provided a method of preparing bioactive molecule coated microcrystals, which crystals display a delayed and/or prolonged release profile in water and/or aqueous solution, comprising the steps of:

(a) providing an aqueous solution comprising coprecipitant molecules and bioactive molecules, wherein the aqueous solution further comprises a source of a first salt;

(b) providing a solvent solution comprising a water miscible organic solvent;

(c) mixing said aqueous solution with said solvent solution such that coprecipitation of the coprecipitant and the bioactive molecules is initiated, resulting in formation of aqueous soluble microcrystals comprising bioactive molecules and the first salt coated on a coprecipitant comprising core; and (d) contacting a water miscible organic solvent comprising a solution of a second salt or a metal complex with the suspension comprising microcrystals obtained in step (c) so as to form a coating of a third salt on the surface of the microcrystals, formed from the double decomposition of said first and second salts or complexes.

The present invention is therefore based on the development of a process to provide water soluble/aqueous solution soluble bioactive molecule coated microcrystals which comprise a further coating on the surface of the bioactive molecule surface, which coating is designed to delay or prolong the release of the bioactive molecule in an aqueous environment e.g. when delivered subcutaneously, intramuscularly, intradermally or via the nose or lung or other mucosal routes to a cell, within a body, or some other aqueous solution including a cleansing liquid. Surprisingly, the double decomposition reaction used to generate the outer coating of inorganic salt was found to be straightforward to carry out within a water-miscible organic solvent. This despite the fact that one component of the reaction generally has only very low solubility in the solvent and is typically present as a precipitate (e.g. $Na_2HPO_4$). Solid-state reactions at ambient temperature typically only occur extremely slowly, if at all, and any biomolecule present would therefore be anticipated to be denatured by the solvent during such a process. The inventors have unexpectedly found that sustained release particles can be prepared in a water miscible organic solvent in less than an hour and that biomolecules remain substantially in a native state during the process.

It should be noted that the first aqueous solution may be provided by mixing two aqueous solutions, one aqueous solution comprising the bioactive molecules and the other aqueous solution comprising the coprecipitant molecules. Alternatively, the bioactive molecule may be provided in an aqueous solution of coprecipitant. Typically, the coprecipitant may be prepared as a substantially saturated or highly concentrated solution. Following mixing with the bioactive molecule the coprecipitant will typically be at between 5 and 100% of its aqueous saturation solubility. Preferably it will be between 20 and 80% of its saturation solubility.

Many of the solutions, solvents, bioactive materials, methods etc. are essentially as described previously in earlier applications. WO 0069887, WO 04/062560 and WO 96/010921, to which the skilled reader is directed and are hereby incorporated by reference, but some features are specifically mentioned herein, but this is not to be construed as limiting.

It is to be understood that the first salt is generally soluble in the aqueous solution and sparingly soluble in the organic solvent and the second salt or complex is generally a metal salt/complex and is soluble in the particular organic solvent used. However, when the organic solvent soluble salt or complex come into contact with the solvent insoluble salt associated with the bioactive molecule coated microcrystals, double decomposition occurs so as to generate a resulting metal salt which is insoluble or sparingly soluble in both the organic solvent and aqueous solution and which forms a coating on the surface of the bioactive molecule microcrystals. The first aqueous soluble salt typically contains a polyvalent anion and the second solvent-soluble salt or complex typically contains a polyvalent metal cation. Typically the organic solvent used for the precipitation in step c) and the coating in step d) comprise the same solvent.

Generally therefore, the metal salt coated on the surface of the bioactive molecule coated microcrystals is a water-insoluble, sparingly soluble or poorly water-soluble metal salt, which serves to delay release of the water soluble bioactive molecule into water/aqueous solution. On delivery of the particles into a living organism the coating may also advantageously serve to prevent degradation of bioactive molecules by enzymes such as proteases or nucleases.

Depending on the particular requirements for a given application, said insoluble/poorly soluble salt can be chosen in order to provide the desired release requirements for the bioactive molecule. It is to be understood that the aqueous solubility of the metal salt coated on the surface of the microcrystals will generally effect the subsequent release of the bioactive molecule.

Suitable metal salts which may be coated on the surface of the microcrystals include metal phosphates, metal carbonates and metal hydroxides which display a degree of insolubility or reduced solubility in water and/or aqueous solutions. Examples include calcium phosphate, calcium pyrophosphate, aluminium hydroxide, aluminium phosphate, calcium carbonate, iron hydroxide, magnesium phosphate, magnesium carbonate and zinc phosphate and combinations of these. The metal salt may be present in an amorphous state or be partially or fully crystalline.

The skilled reader can easily determine a suitable combination of first and second metal salts which may be appropriate for generating the above water insoluble/poorly soluble metal salts. Exemplar pairs include the water soluble $Na_2HPO_4$ (or $NaH_2PO_4$) combined with organic soluble $CaCl_2$ to generate a coating comprising one or more calcium phosphate salts, or $K_2HPO_4$ (or $KH_2PO_4$) and $CaCl_2$ to generate a coating comprising one or more calcium phosphate salts. Calcium salts that may be produced include $CaHPO_4$, $Ca(H_2PO_4)_2$, $Ca_3(PO_4)_2$ (tricalcium phosphate), $Ca_2P_2O_7$, and $Ca_5(PO_4)_3OH$ (hydroxyapatite).

In a further aspect there is provided water/aqueous solution soluble microcrystals comprising a coprecipitant core material and a bioactive molecule coating thereon, wherein the microcrystals further comprise an outer coating of an insoluble, sparingly soluble or poorly water/aqueous solution soluble metal salt for delaying and/or prolonging release and dissolution of the bioactive molecule in water and/or an aqueous solution and/or within natural organisms.

In accordance with the present invention, the dissolution of the bioactive molecule in water and/or an aqueous solution is delayed and/or prolonged. It is to be understood that this is in reference to microcrystals which do not comprise a water insoluble/poorly soluble metal salt outer coating. Microcrystals which do not comprise such a metal salt outer coating can generally dissolve in water/aqueous solution in a matter of seconds or minutes. The microcrystals of the present invention, which comprise a metal salt outer coating display a delayed and/or prolonged dissolution profile of the bioactive molecule. Generally the delay in dissolution of the bioactive molecule may by hours or days or weeks, for example 0-48 hours or 0-240 hrs. The prolonged dissolution profile can result in the bioactive molecule being released and subsequently dissolved also over a period of hours or days, for example 1-48 hours. Through appropriate choice of metal salt and concentration, the skilled addressee can tailor the release profile for any desired application. For example, for drug administration, it may be desirable to provide microcrystals which are capable of releasing the bioactive molecule over several hours, such as 2-24 hours, e.g. 4-12 hours. Similarly for vaccination it may be desirable for an antigen to be released very slowly or for there to be an initial release of some of the antigen with only slow dissolution of the remaining particles. Through routine optimisation, the skilled addressee can provide microcrystals which display the appropriate bioactive molecule release profile for a given application.

It is envisaged that delayed/prolonged release microcrystals of the present invention may find use in a variety of applications. However, perhaps the most relevant application will be in the fields of drug delivery or vaccine delivery, where it may be desirable to be able to deliver a drug or immune stimulating agent over a period of hours or days.

For example where hitherto, a drug may have to have been administered, by for example injection, at a number of time points in a day, it may now be possible to utilise a microcrystal of the present invention in order to prolong and/or continually release a particular drug and reduce the number of times a drug has to be administered for example by reducing the number of painful injections. Indeed, this can be more efficient such that less drug may have to be administered to a subject.

In terms of vaccine delivery, prolonged release or delayed release may be desirable in order to enhance an immune response. Indeed, particles of the present invention may be administered to a subject conjointly with particles which do not comprise the outer coating of metal salt. In this manner a subject may get a desirable double administration (i.e. at a first and second time point) of bioactive molecule, such as an antigenic protein, which may be efficacious for eliciting a good immune response. Moreover, if the outer coating is formed from aluminium hydroxide or calcium phosphate, an adjuvant effect may also be provided.

In order to produce vaccines it is preferable to use physiologically acceptable carriers with low water solubility such as amino-acids like histidine, glutamine and asparagine. This is because these allow higher particle loadings to be achieved for antigens and/or adjuvants that are typically only available at low concentration. For administration dry particles need to be readily resuspendable into an aqueous diluent and for dosing into vials should preferably be free-flowing. Sustained release particles formed by coating bioactive molecule coated glutamine or asparagine crystals with a layer of calcium phosphate are found to fulfil these criteria and are therefore highly preferred. Preparation of vaccines of this type is preferably carried out using an aqueous phosphate buffered solutions of the antigen/adjuvant and a calcium salt dissolved in an organic solvent such as isopropanol or 2-methylpropanol. To be able to isolate the particles as free-flowing powders with useful sustained release characteristics the aqueous phosphate buffer may preferably be used at a concentration of 5-100 mM and the concentration of calcium salt in the excess solvent may be 2-25 mM. Most preferably a sodium phosphate buffer may be used at a concentration of 20-75 mM with a concentration of 5-15 mM calcium chloride in the solvent. To ensure good sustained release characteristics the percentage of water in the suspension following precipitation will preferably be 3-9% v/v. The dry isolated particles thus formed will typically contain 2-20% w/w calcium phosphate salts and preferably 5-15% w/w calcium phosphate salts. A low weight percentage of low solubility material in the particles may be advantageous because it means that there will be less material to be cleared on administration to living organisms.

For applications where the bioactive molecule is available at high concentrations it may be preferable to use a higher solubility physiologically acceptable carrier such as glycine. To obtain useful sustained release characteristic using glycine, the preferred aqueous phosphate concentrations are higher and may be 20-150 mM while the calcium chloride concentrations in solvent may be 5-40 mM. To ensure high reproducibility and scalability the manufacture of the sustained release formulations is preferably carried out using a continuous precipitation and coating process.

As well as drug/vaccine delivery, the microcrystals of the present invention may find application as long acting antifouling agents, enzyme use, for example in cleaning applications, long acting antibacterial or bactericidal administration and the like. For example, prolongation of dissolution times may be achieved by including a common ion in the aqueous solution—e.g. concentrated phosphate ions in cleansing applications—resulting protein release is triggered by a dilution process.

The coprecipitant must be sufficiently soluble in the aqueous solution such that a suitable weight fraction may be obtained relative to the bioactive molecule in solution. Preferably, the coprecipitant has a substantially lower solubility in the miscible organic solvent than in the aqueous solution. The concentration of coprecipitant required is a function of the amount of bioactive molecule in the solution and the molecular mass of the bioactive molecule.

The skilled addressee will appreciate that the coprecipitant should be chosen so that it does not substantially react and/or cause an adverse reaction with the bioactive molecule.

The bioactive/coprecipitant solution is admixed with a substantially water miscible organic solvent or water miscible mixture of solvents, preferably one where the solvent or solvent mixture is substantially fully miscible. Typically, the bioactive molecule/coprecipitant solution is added to an excess of water miscible organic solvent. The excess of fully water miscible organic solvent is such that the final water content of the solvent/aqueous solution is generally less than 30%, typically less than 10-20 vol % and conveniently less than 8 vol %. In this manner, the organic solvent should preferably initially contain less than 0.5-5 vol % water or be substantially dry, but may not necessarily be completely dry.

Typical water miscible organic solvents may, for example, be: ethanol; propan-1-ol; propan-2-ol; acetone, ethyl lactate, tetrahydrofuran, 2-methyl-propanol, 2,4-pentanediol, 1,5-pentane diol, and various size polyethylene glycol (PEGS) and polyols; or any combination thereof. Preferred solvents and mixtures will have suitable viscosities for efficient mixing with good retention of biomolecule integrity In certain circumstances, the organic solvent may be presaturated with the bioactive molecule and/or coprecipitate to ensure that on addition of the aqueous solution the two components precipitate out together.

It should be understood that the term "mixing" refers to a process step wherein the water miscible solvent is mixed or agitated with the aqueous solution while the aqueous solution is added thereto. The mixing needs to be efficient so that the bioactive molecule is in contact with a mixture of intermediate composition i.e. aqueous solution and organic solvent, for example, between 25% and 60% solvent, for a minimal time. Thus, the aqueous solution may be added to the organic solvent using a wide range of methods such as a continual stream, spray or mist. Preferably the mixing of the bioactive molecule and coprecipitate solution may occur in a process wherein a continuous stream of bioactive molecules and coprecipitate are mixed together with an amount of solvent.

A continuous, as opposed to batch-wise co-precipitation process is advantageous and this may operate by mixing together two or more continuous streams. Thus a continuous stream of water miscible organic solvent or mixture of solvents may be mixed with a continuous aqueous stream comprising a bioactive molecule/co-precipitant solution in, for example, a dynamic or static mixing device such as an impinger, macromixer, micromixer or in-line tube mixer. The water miscible solvent stream may contain water at less than 5 vol % and/or be substantially saturated with coprecipitant to aid coprecipitation. The aqueous stream or solvent stream may also contain other excipients typically employed in pharmaceutical formulations such as buffers, salts and/or surfactants and precipitation stabilising compounds. Surfactants will typically dissolve in the water miscible solvent and not be incorporated into the particles. The co-precipitation process may be initiated in the mixing chamber with the formed particles or precursors flowing out to produce a suspension in the mixed solvent stream to be collected in a holding vessel. The particles produced by such a static or dynamic mixing process have been found to be substantially consistent in size, shape and yield. Advantageously this continuous process may be carried out over a wide temperature range including temperatures between 0° C. and ambient temperature as well as elevated temperatures.

The suspension of coprecipitated bioactive molecule coated microcrystals in the aqueous-water miscible solvent mixture may be combined with the solvent containing the second salt via a batch mixing process or via a continuous mixing process. The continuous mixing process may be simultaneous with or follow directly on from the coprecipitation step such that the suspension of microcrystals resulting from the first continuous mixing device forms the feed into a second mixing device where they are combined with a solution of the second salt in solvent. Alternatively the microcrystals formed in the coprecipitation step may be collected and treated with the second salt after a delay of minutes or hours either via a batch or continuous mixing process. The suspension of biomolecule coated microcrystals combined with the organic solvent solution of the second salt will typically be held in a collecting vessel for a known period of time before the microcrystals are removed from the solvent. This provides for the ion exchange process, required to form the third insoluble salt on the surface of the microcrystals, to move towards completion. Varying the time period can therefore be used to alter the solubility properties of the resultant particles with longer exposure periods typically leading to particles that exhibit slower release. It may be beneficial to agitate the suspension of microcrystals and typically the process will reach completion after about 0.5-5 hours.

In the continuous co-precipitation system one pump may continuously deliver aqueous solution containing concentrated coprecipitant and bioactive molecule while another pump may deliver the solvent phase which may optionally comprise the second metal salt. Further pumps/stream may be used to provide the further solvent solution comprising the second metal salt.

The pumps may be of many different kinds but must accurately deliver the solutions at a defined flow rate and be compatible with the bioactive molecules employed. Conveniently, HPLC, gear or peristaltic pumps or the like can be used since these are optimised for delivering aqueous solutions and water miscible solvents over a range of flow rates. Typically, the aqueous solution will be delivered at flow rates between 10 ml/min and 2 l/min. The aqueous pump head and lines or peristaltic tubing may be made of material that resists fouling by the bioactive molecule. The solvent may generally be delivered 4-100 times faster than the aqueous and so a more powerful pump such as a gear or centrifugal pump may be required. Typically the solvent may be delivered at between 200 ml/min and 40 l/min.

A mixing device may provide a method for rapidly and intimately mixing a continuous aqueous stream with a continuous water miscible solvent stream such that the precipitation process begins to occur almost immediately.

The mixing device may be any device that achieves rapid mixing of the two flows. Thus it can, for example, be a static device that operates by shaping/combining the incoming liquid flow patterns or else a dynamic device that actively agitates the two fluid streams together. Preferably, it is a static device. Within a dynamic device agitation of the two streams may be achieved by use of a variety of means such as stirring, sonication, shaking or the like. Methods of stirring include a paddle stirrer, a screw and a magnetic stirrer. If magnetic stirring is used a variety of stirring bars can be used with different profiles such as, for example, a simple rod or a Maltese cross. A wide variety of static mixing devices may be suitable for combining the aqueous and solvent streams or the two different solvent streams including impingers, macromixers, tube mixers and micromixers. Static devices include T-mixers, cross-mixers, Y-mixers and in-line tube mixers such as a Kenics mixer and may have two or more inlets. Preferred devices will be those that provide for a chaotic type of mixing regime rather than a diffusional type mixing regime. The material lining the interior of the mixing device may preferably be chosen to prevent significant binding of the bioactive molecule or the particles onto it. Suitable materials may include 316 stainless steel, titanium, silicone and Teflon (Registered Trade Mark).

Depending on the production scale required the mixing device may be produced in different sizes and geometries. The size of the mixing device required is a function of the rate of flow of the two solvent streams. Typically, in a continuous process the bioactive/coprecipitate solution is added to an excess of water miscible organic solvent. This entails the smaller volume of bioactive molecule/coprecipitate solution being added to the larger volume of the excess of organic solvent such that rapid dilution of water from the bioactive molecule/coprecipitate solution into the organic solvent occurs with an accompanying rapid dehydration of the bioactive molecule and formation of particles according to the first aspect. The temperature at which the precipitation is carried out may be varied. For example, the aqueous solution and the solvent may be either heated or cooled. Cooling may be useful where the bioactive molecule is fragile. Alternatively, the solvent and aqueous mixtures may be at different temperatures. For example, the solvent may be held at a temperature below the freezing point of the aqueous mixture. Moreover, the pressure may also be varied, for example, higher pressures may be useful to reduce the volatility of the solvent.

Upon admixing the bioactive molecule/coprecipitant solution, to the excess of the water miscible organic solvent, precipitation of the bioactive and coprecipitant typically starts to occur substantially instantaneously. The appearance of visible particles may however take several minutes.

The precipitated particles are coated with a water insoluble/poorly soluble metal salt by mixing an organic solvent containing low amounts of water and comprising the second metal salt.

With time the metal salt coated microcrystals will settle, which allows easy recovery of a concentrated suspension of particles by decanting off excess solvent. The microcrystals may, however, be subjected to, for example, centrifugation and/or filtration in order to more rapidly recover them. Conventional drying procedures known in the art such as air drying, vacuum drying or fluidised bed drying may be used to evaporate any residual solvent to leave solvent free microcrystals.

Alternatively, solvent may be removed from the particles in a drying procedure using supercritical or liquid $CO_2$ or other inert liquefied or supercritical gases such as hydrofluorocarbons. Such a technique removes virtually all residual solvent from the particles. This is of particular benefit for pharmaceutical formulation since residual solvent may lead to unexpected physiological effects.

For pharmaceutical applications dry precipitated particles may be typically introduced into a sterile delivery device or vial under sterile conditions prior to use. Alternatively the particles may be transferred into the sterile delivery device or vial as a suspension in solvent or liquefied gas under sterile conditions. They may then be optionally dried in situ using for example supercritical $CO_2$ or liquefied gas drying.

The formulations described in the invention may typically be produced at a number of dosage strengths. The dosage may be conveniently varied by varying the percentage weight of bioactive molecule per microcrystal from below 0.1 wt % up to about 50 wt %.

Typically the methods and microcrystals described herein may span a narrow size distribution with a mean particle size of less than 50 microns, such as less than 25 µm or 10 µm. Formulations containing a narrow size distribution of coated crystals provide improved delivery reproducibility and hence better clinical performance. The microcrystals are generally larger than 100 nm in diameter For vaccines the particles will preferably have a mean size in the range 2-25 microns and most preferably 3-12 microns so they may be efficiently taken up by antigen presenting cells.

The pharmaceutical formulations described can be conveniently produced in a sterile form by pre-filtering the aqueous and organic solutions through 0.2 micron filters prior to admixing them in a contained sterile environment. Pharmaceutical formulations should be substantially free of harmful residual solvents and this invention typically provides powders containing less than 0.5 wt % of a Class 3 solvent following conventional drying procedures. Substantially lower solvent levels are obtainable by flowing supercritical fluid $CO_2$ through a suspension of the crystals in a dry water miscible and $CO_2$ miscible solvent.

The method may also be used to make bioactive molecule coated microcrystals suitable for pharmaceutical formulations using water-soluble bioactive compounds that are much smaller than typical biological macromolecules. These formulations may be made either by a batch or a continuous process and may advantageously employ a non-hygroscopic carrier such as D,L-valine. Water-soluble antibiotic drugs such as tobramycin sulphate and other water-soluble bioactive molecules may be used. Preferably, the bioactive molecule may be polar and contain one or more functional groups that is ionised at the pH used for coprecipitation. The bioactive molecule should also preferably have a largest dimension greater than that of the unit cell formed by the core material on crystallisation. This will favour formation of bioactive molecule coated microcrystals and minimise the possibility of inclusion of the bioactive molecule within the crystal lattice.

By microcrystal is meant that the constituent molecules or ions are organised into a solid 3-dimensional crystal lattice of repeating symmetry that remains substantially unchanged on heating until a well-defined melting transition temperature is reached. Conveniently, the coprecipitant forms a crystalline core with a high degree of crystallinity. Typically, a well-defined melting endotherm (i.e. not a glass transition) may be observed on heating the particles in a differential scanning calorimeter (DSC). This is a well-known characteristic showing crystallinity and also shows that the crystalline core may be generally substantially composed of solid-state phases that are thermodynamically stable at room temperature and ambient humidity. The microcrystals according to the present invention may also show birefringence which is also a characteristic of crystallinity. The particles may also shown an X-ray diffraction pattern which is yet again evidence of crystallinity.

Typically, when preparing high dosage formulations the coating of bioactive molecules may be substantially continuous. Alternatively, for vaccines it may be advantageous to have a pharmaceutical formulation comprising particles with a substantially discontinuous coating of bioactive molecules. The inorganic material will form a coating that slows the dissolution of the bioactive molecules. The pharmaceutical formulation may desirably comprise particles with a narrow size distribution. Typically, the pharmaceutical formulation may therefore comprise a substantially homogeneous system with a significant number of particles having generally the same or similar size.

The microcrystals may have a maximum cross-sectional dimension of less than about 80 μm, preferably less than 50 μm across or more preferably less than 20 μm. By maximal cross-sectional dimension is meant the largest distance measurable between the diametrically opposite points.

The molecules which make up the crystalline core may, for example, be: amino acids, zwitterions, peptides, sugars, buffer components, water soluble drugs, organic and inorganic salts, compounds that form strongly hydrogen bonded lattices or derivatives or any combinations thereof.

Amino acids suitable for forming the crystalline core may be in the form of pure enantiomers or racemates, Examples include: alanine, arginine, asparagine, glycine, glutamine, histidine, lysine, leucine, isoleucine, norleucine, D-valine, L-valine, mixtures of D,L-valine, methionine, phenylalanine, proline and serine or any combination thereof. In particular, glycine, L-alanine, L-glutamine, L-histidine, L-serine, L-methionine, L-asparagine, D,L-asparagine, L-proline, L-valine or D,L-valine are preferred. For amino-acids that have side-chains that substantially ionise under coprecipitation conditions it is preferable to use counterions that generate crystalline salts with low solubility and which are non-hygroscopic. Examples of other molecules and salts for forming the crystalline core may include, but are not limited to α-lactose, β-lactose, mannitol, ammonium bicarbonate, sodium glutamate, arginine phosphate and betaines. A preferred sugar alcohol is myoinositol.

Conveniently, bioactive molecules forming a coating on the crystalline core may be selected from any molecule capable of producing a desired, therapeutic effect such as for example an active pharmaceutical ingredient (API) or diagnostic effect. By therapeutic effect is meant any effect which cures, alleviates, removes or lessens the symptoms of, or prevents or reduces the possibility of contracting any disorder or malfunction of the human or animal body and therefore encompasses prophylactic effects.

The coating of bioactive molecules may also comprise excipients commonly used in pharmaceutical formulations such as stabilizers, surfactants, isotonicity modifiers and pH/buffering agents. It should be understood that solvent soluble excipients such as surfactants will not be incorporated into the particles and will remain in the solvent Preferably, the core and/or coating of the microcrystals are free or substantially free of polymeric material. Desirably therefore the microcrystals, except for the bioactive molecules themselves, are formed from non-polymeric compounds which are less than 100 Da, preferably 50 Da.

The bioactive molecules may, for example, be: any drug, peptide, polypeptide, protein, nucleic acid, sugar, vaccine component, adjuvant or any derivative thereof or any combination which produces a therapeutic effect.

Examples of bioactive molecules include, but are not limited to drugs such as: anti-inflammatories, anti-cancer, anti-psychotic, anti-bacterial, anti-fungal; natural or unnatural peptides; proteins such as insulin, α1-antitrypsin, α-chymotrypsin, albumin, interferons, antibodies; nucleic acids such as fragments of genes, DNA from natural sources or synthetic oligonucleotides and anti-sense nucleotides; sugars such as any mono-, di- or polysaccharides; and plasmids.

Nucleic acids may for example be capable of being expressed once introduced into a recipient. The nucleic acid may thus include appropriate regulatory control elements (e.g. promoters, enhancers, terminators etc) for controlling expression of the nucleic acid. The bioactive molecule may also be a chemically modified derivative of a natural or synthetic therapeutic agent such as a PEG-protein.

The nucleic acid may be comprised within a vector such as a plasmid, phagemid or virus vector. Any suitable vector known to a man skilled in the art may be used.

Vaccine coating components may, for example, include antigenic components of a disease causing agent, for example a bacterium or virus, such as diptheria toxoid and/or tetanus toxoid. Vaccines are useful for the prevention and/or treatment of infections caused by pathogenic micro-organisms, including viral, fungal, protozoal, amoebic and bacterial infections and the like. Examples of vaccine formulations that can be prepared according to the present invention include sub-unit, attenuated or inactivated organism vaccines including, but not limited to, recombinant protective antigen (anthrax), diphtheria, tetanus, polio, pertussus and hepatitis A, B and C, HIV, rabies, measles, mumps, dengue, rotavirus, rubella, yellow fever and influenza. It is also possible to use vaccine components based on DNA, including plasmids, viral and viral-like particles and polysaccharides and conjugates thereof.

Additionally, an adjuvant may be provided to enhance the immunogenicity of the particular antigenic component. Many such adjuvants are know to the skilled addressee, including aluminium and calcium salts, monophosphoryl lipid A, CpG oligonucleotides, cholera toxin and heat labile toxin from *Escherichia coli* and lipoproteins. Synthetic oligodeoxynucleotides containing unmethylated CpG motifs, for example, act as immune adjuvants, accelerating and boosting antigen-specific antibody responses by up to 500-fold. CpG motifs promote the production of T-helper and pro-inflammatory cytokines and induce the maturation/activation of professional antigen-presenting cells (including macrophages and dendritic cells). These effects are optimized by maintaining close physical contact between the CpG DNA and the immunogen. Coadministering CpG DNA with a variety of vaccines has improved protective immunity in animal challenge models. Ongoing clinical studies indicate that CpG oligodeoxynucleotides are safe and well-tolerated when administered as adjuvants to humans and in some cases increase vaccine-induced immune responses.

In addition vaccine component coated micro-crystals may be useful for formulation of vaccines developed for cancers, especially human cancers, including melanomas; a skin cancer; lung cancer; breast cancer; colon cancer and other cancers. Pulmonary formulations as described herein may be particularly suited for treatment of lung cancer.

The amount of bioactive molecule coated onto each particle can be conveniently varied by changing the ratio of bioactive molecule to core molecule in the initial aqueous solution prior to coprecipitation. Typically the bioactive molecule will make up between about 0.01 wt % and 50 wt % of each coated microcrystal. More preferably the loading of bioactive molecule in the particles will be between 0.1 wt % and 35 wt %.

Typically, at least some of the bioactive molecules retain a high level of activity even after exposure to high humidity.

Typically, the bioactive molecules coated on the crystalline core retain a native or near-native configuration i.e. the bioactive molecules are not irreversibly denatured during the production process. Coating of the bioactive molecules onto the crystalline core is also advantageously found to lead to enhanced stability on storage of the particles at ambient or elevated temperatures. For example, typically the bioactive molecule may retain most of its bioactivity when reconstituted in aqueous media. Preferably the bioactive molecule will retain greater than 50% of it's initial bioactivity after storage at 25 C for 6 months. More preferably the bioactive molecule will retain greater then 80% of its bioactivity and most preferably greater than 95% bioactivity.

Commonly bioactive molecules require excipients or stabilising agents to be present when dissolved in aqueous solution such as buffer compounds, salts, sugars, surfactants and antioxidants. These may be included in the starting aqueous solution and incorporated into the particles during the coprecipitation process. They will then be present on reconstitution of the particles for example as a pharmaceutical formulation. Typically following coprecipitation of all the solvent insoluble components the excipients will be concentrated on the outer surface of the particle and will permeate into the coating of bioactive molecules. A typical antioxidant may, for example, be cysteine such as in the form of N-acetyl cysteine. In order to use inhalation to administer drug molecules into the bloodstream, the drug must be made into a formulation capable of being delivered to the deep lung. In the case of dry-powder, this generally requires particles with mass median dimensions in the range 1-5 microns, although it has been demonstrated that larger particles with special aerodynamic properties may be used. Certain formulations of microcrystals according to the present invention are suitable for forming pulmonary formulations as they can be used to generate fine free-flowing microcrystals well suited to delivery by inhalation. Given that the bioactive molecule is on the surface of these non-hygroscopic coated microcrystals, the particles generally exhibit unexpectedly low static charge and are straight-forward to handle and use in a delivery device as a dry powder. Alternatively, for example, they can be used as a suspension in a nebulisor. In particular, bioactive molecules suitable for the formation of pulmonary pharmaceutical formulations may include but are not restricted to any of the following: therapeutic proteins such as insulin, α1-antitrypsin, interferons; antibodies and antibody fragments and derivatives; therapeutic peptides and hormones; synthetic and natural DNA including DNA based medicines; enzymes; vaccine components; antibiotics; pain-killers; water-soluble drugs; water-sensitive drugs; lipids and surfactants; polysaccharides; or any combination or derivatives thereof. The pulmonary formulation comprising particles may be used directly in an inhaler device to provide high emitted doses and high fine particle fractions. Thus emitted doses measured in a MSLI (stages 1-5) are typically greater than 70%. The fine particle fractions measured in a MSLI (stages 3-5) are typically greater than 20% and preferably greater than 50%. The fine particle fraction is defined as the fraction collected on the lower stages of a multi-stage liquid impinger (MSLI) and corresponds to particles with aerodynamic properties suitable for administration to the deep lung by inhalation i.e. less than about 3.3 microns. The pulmonary formulation may be used in a dry powder delivery device without any further formulation with, for example, larger carrier particles such as lactose. Dry powder vaccines delivered by inhalation may be used to provide stable vaccines with no requirement for cold chain. Delivery to the deep lung may provide enhanced immunogenicity with more rapid immune onset and result in a mucosal immune response. Delivery by inhalation provides for the possibility for rapid mass vaccination campaigns, via self administration and for improved compliance where boosters are required.

For pulmonary formulations, microcrystals with a mass median aerodynamic diameter less than 10 microns and more preferably less than 5 microns are preferred. These will typically have a mass median diameter similar to their mass median aerodynamic diameter. Typically free-flowing, non-hygroscopic low static microcrystals with maximum cross-sectional diameters in the range of 1-5 microns are preferred. These can be obtained using amino-acids such as for example, L-glutamine to form the crystalline core. However, the inventors have surprisingly discovered that bioactive molecule coated particles that take the form of high aspect ratio flakes may advantageously have mass median aerodynamic diameters smaller then their maximum cross-sectional diameters. Suitable shapes may be, for example, leaf shaped or tile shaped. With such microcrystals the preferred range of maximum cross-sectional diameters may be greater than 1-5 microns and may for example be 1-10 microns. Coprecipitants which typically form bioactive molecule coated crystalline particles of this shape include histidine, and D,L-valine. For dry powder pulmonary formulations, microcrystals made with coprecipitants that produce high aspect ratio flakes are therefore also preferred. For certain coprecipitants agglomerates of microcrystals may be formed which typically exhibit mass median aerodynamic diameters smaller then their maximum cross-sectional diameters. Particles formed from agglomerates typically have an overall spherical shape and form free-flowing powders. Examples of coprecipitants that may form agglomerates include glycine, valine and glycine.

In particular, pulmonary formulations may preferably be selected to have crystalline cores comprised of amino-acids such as valine, histidine, isoleucine, glycine or glutamine. It is preferred when forming the particles for the formulation that co-preciptants are used which give discrete microcrystals or agglomerates which do not aggregate into larger particles on exposure to high humidity. In addition it is preferable that the coprecipitant does not leave an unpleasant taste in the patients mouth following administration. Glutamine is therefore highly preferred since it can be exposed to high humidity and has a bland taste.

Bioactive molecules suitable for administration by parenteral delivery include those described above. In addition parenteral administration can be used to deliver larger biomolecules such as antibodies not suited to administration into the subject's blood-stream via the lung because of poor systemic bioavailability. Preferred crystalline core materials include excipients commonly used in parenteral formulations such as glycine and mannitol. Also preferred are natural amino-acids such as L-glutamine and natural sugar alcohols such as myoinositol that can be used to form particles that reconstitute rapidly, are stable even at high temperature and are easy to process and handle. L-glutamine is also preferred because it has been administered to patients at high dosages with no adverse side-effects.

Those skilled in the art will realise that using combinations of the above teaching it is possible to provide other pharmaceutical formulations such as for example nasal formulations, oral formulations and topical formulations. Nasal formulations and oral formulations may require coating of the particles with alternate materials that provide adhesion to for example mucosal membranes.

The present invention will now be described by way of non-limiting example.

EXAMPLES SECTION

Example 1

Preparation of Calcium Phosphate (Cap) Modified Protein Coated Microcrystals (PCMC)

To demonstrate the applicability of the invention CaP modified PCMC were prepared using bovine serum albumin (BSA) and a range of core crystalline coprecipitants. Unmodified PCMC were also prepared using the same crystalline coprecipitants so that their solubility characteristics could be compared. Samples were prepared at acidic and basic pH, using different concentrations of phosphate buffer in the aqueous phase and different concentrations of calcium chloride in the solvent phase. The average particle size within the dry powders and the release of protein following reconstitution into aqueous buffer were measured, using a Helios machine from Sympatec, Clausthal-Zellerfeld, Germany, according to manufacturers protocols.
Preparation of Samples
CaPat1-86-001:
Soluble and Slow Release BSA/Gln PCMC precipitated into propan-2-ol, Theoretical protein loading (TPL)=16.7% w/w, 50 mM $NaH_2PO_4$, 10 mM $CaCl_2$, pH ~4

20 mg BSA was dissolved in 5 ml of aqueous glutamine (Gln) (20 mg/ml) containing 50 mM $NaH_2PO_4$.

4 ml of this solution was added dropwise using a 1 ml pipette into 70 ml of propan-2-ol (Pr2OH) with rapid mixing using a magnetic stirrer. 37 ml of this suspension was removed immediately (while mixing), and soluble crystals isolated from the supernatant by filtration onto a membrane filter and dried overnight in air (soluble sample).

To the remaining 37 ml of suspension, 5 ml of $CaCl_2$ dissolved in Pr2OH was added in 1 lot and mixed for 2 min (final conc of 10 mM $CaCl_2$). The magnetic stirring bar was removed, and the sample transferred to a Vibrax-VXR (speed 800) and shaken for 1 hr.

The CaP modified slow release crystals were isolated from the supernatant by filtration onto a membrane filter, washed with 10 ml of dry Pr2OH and dried overnight in air.

The remaining soluble and slow release samples were prepared according to similar protocols as summarised below.
CaPat1-86-002
Soluble and Slow Release BSA/Val PCMC made in Pr2OH, TPL=16.7% w/w 50 mM $NaH_2PO_4$, 10 mM $CaCl_2$, pH ~4

44 mg BSA dissolved in 4.4 ml valine (50 mg/ml) in 50 mM $NaH_2PO_4$.

4 ml added dropwise by 1 ml pipette into 70 ml of Pr2OH with mixing.

37 ml removed immediately (while mixing), filtered and dried overnight in air (soluble sample).

To remaining 37 ml of suspension, 5 ml of $CaCl_2$ in Pr2OH added in 1 lot and mixed for 2 min (final conc of 10 mM $CaCl_2$).

Magnetic stirring bar removed, and bottle transferred to Vibrax-VXR (speed 800) for 1 hr.

Crystals filtered, washed with 10 ml of dry Pr2OH and dried overnight in air.
CaPat1-86-003
Soluble and Slow Release BSA/Myoinositol PCMC made in Pr2OH, TPL=16.7% w/w
50 mM $NaH_2PO_4$, 10 mM $CaCl_2$, pH ~4

44 mg BSA dissolved in 4.4 ml myoinositol (50 mg/ml) in 50 mM $NaH_2PO_4$.

4 ml added dropwise by 1 ml pipette into 70 ml of Pr2OH with mixing.

37 ml removed immediately (while mixing), filtered and dried overnight in air (soluble sample).

To remaining 37 ml of suspension, 5 ml of $CaCl_2$ in Pr2OH added in 1 lot and mixed for 2 min (final conc of 10 mM $CaCl_2$).

Magnetic stirring bar removed, and bottle transferred to Vibrax-VXR (speed 800) for 1 hr.

Crystals filtered, washed with 10 ml of dry Pr2OH and dried overnight in air.
CaPat1-86-004
Soluble and Slow Release BSA/Gly PCMC made in Pr2OH, TPL=16.7% w/w
50 mM $NaH_2PO_4$, 10 mM $CaCl_2$, pH ~4

88 mg BSA dissolved in 4.4 ml glycine (100 mg/ml) in 50 mM $NaH_2PO_4$.

4 ml added dropwise by 1 ml pipette into 70 ml of Pr2OH with mixing.

37 ml removed immediately (while mixing), filtered and dried overnight in air (soluble sample).

To remaining 37 ml of suspension, 5 ml of $CaCl_2$ in Pr2OH added in 1 lot and mixed for 2 min (final conc of 10 mM $CaCl_2$).

Magnetic stirring bar removed, and bottle transferred to Vibrax-VXR (speed 800) for 1 hr.

Crystals filtered, washed with 10 ml of dry Pr2OH and dried overnight in air.
CaPat1-86-005
Soluble and Slow Release BSA/Ala made in Pr2OH), TPL=16.7% w/w
50 mM $NaH_2PO_4$, 10 mM $CaCl_2$, pH ~4

132 mg BSA dissolved in 4.4 ml alanine (150 mg/ml) in 50 mM $NaH_2PO_4$.

4 ml added dropwise by 1 ml pipette into 70 ml of Pr2OH with mixing.

37 ml removed immediately (while mixing), filtered and dried overnight in air (soluble sample).

To remaining 37 ml of suspension, 5 ml of $CaCl_2$ in Pr2OH added in 1 lot and mixed for 2 min (final conc of 10 mM $CaCl_2$).

Magnetic stirring bar removed, and bottle transferred to Vibrax-VXR (speed 800) for 1 hr.

Crystals filtered, washed with 10 ml of dry Pr2OH and dried overnight in air.
CaPat1-76-001:
Soluble and Slow Release BSA/Gln made in Pr2OH, TPL=16.7% w/w
25 mM $Na_2HPO_4$, 5 mM $CaCl_2$, pH ~8

20 mg BSA dissolved in 5 ml glutamine (at 20 mg/ml) in 25 mM $Na_2HPO_4$.

4 ml added dropwise by 1 ml pipette into 70 ml of Pr2OH with mixing.

37 ml removed immediately (while mixing), filtered and dried overnight in air (soluble sample).

To the remaining 37 ml of suspension, 5 ml of CaCl$_2$ in Pr2OH added in 1 lot and mixed for 2 min (final conc of 5 mM CaCl$_2$) Magnetic stirring bar removed, and bottle transferred to Vibrax-VXR (speed 800) for 1 hr.

Crystals filtered, washed with 10 ml of dry Pr2OH and dried in overnight in air.

CaPat1-76-002

Soluble and Slow Release BSA/Val made in Pr2OH, TPL=16.7% w/w 25 mM Na$_2$HPO$_4$, 5 mM CaCl$_2$, pH ~8

44 mg BSA dissolved in 4.4 ml valine (50 mg/ml) in 25 mM Na$_2$HPO$_4$.

4 ml added dropwise by 1 ml pipette into 70 ml of Pr2OH with mixing.

37 ml removed immediately (while mixing), filtered and dried overnight in air (soluble sample).

To the remaining 37 ml of suspension, 5 ml of CaCl$_2$ in Pr2OH added in 1 lot and mixed for 2 min (final conc of 5 mM CaCl$_2$)

Magnetic stirring bar removed, and bottle transferred to Vibrax-VXR (speed 800) for 1 hr.

Crystals filtered, washed with 10 ml of dry Pr2OH and dried overnight in air.

CaPat1-76-003

Soluble and Slow Release BSA/Myoinositol made in Pr2OH, TPL=16.7% w/w 25 mM Na$_2$HPO$_4$, 5 mM CaCl$_2$, pH ~8

44 mg BSA dissolved in 4.4 ml myoinositol (50 mg/ml) in 25 mM Na$_2$HPO$_4$.

4 ml added dropwise by 1 ml pipette into 70 ml of Pr2OH with mixing.

37 ml removed immediately (while mixing), filtered and dried overnight in air (soluble sample).

To the remaining 37 ml of suspension, 5 ml of CaCl$_2$ in Pr2OH added in 1 lot and mixed for 2 min (final conc of 5 mM CaCl$_2$).

Magnetic stirring bar removed, and bottle transferred to Vibrax-VXR (speed 800) for 1 hr.

Crystals filtered, washed with 10 ml of dry Pr2OH and dried overnight in air.

CaPat1-76-004

Soluble and Slow Release BSA/Gly made in Pr2OH, TPL=16.7% w/w 25 mM Na$_2$HPO$_4$, 5 mM CaCl$_2$, pH ~8

88 mg BSA dissolved in 4.4 ml glycine (100 mg/ml) in 25 mM Na$_2$HPO$_4$.

4 ml added dropwise by 1 ml pipette into 70 ml of Pr2OH with mixing.

37 ml removed immediately (while mixing), filtered and dried overnight in air (soluble sample).

To the remaining 37 ml of suspension, 5 ml of CaCl$_2$ in Pr2OH added in 1 lot and mixed for 2 min (final conc of 5 mM CaCl$_2$)

Magnetic stirring bar removed, and bottle transferred to Vibrax-VXR (speed 800) for 1 hr.

Crystals filtered, washed with 10 ml of dry Pr2OH and dried overnight in air.

Results

Unmodified PCMC

All of the unmodified (soluble) PCMC were found to dissolve rapidly into aqueous buffer releasing 90-100% of the BSA protein in less than 5 minutes.

CaP Modified PCMC

The CaP modified PCMC prepared at pH 4 formed suspensions on reconstitution in aqueous buffer and the BSA protein was released slowly from the particles, The amount of protein released after 1 hr and 24 hr was found to be a function of the core crystalline material as shown in Table 1. Also the average particle size within the dry powders, as measured by light scattering, was found to vary with the crystalline core material.

TABLE 1

Slow ReleaseCaP modified BSA PCMC Formulations prepared from various carriers using 50 mM NaH$_2$PO$_4$ (pH ~4) and 10 mM CaCl$_2$

| CARRIER | PROTEIN RELEASED (%) at | | SYMPATEC X$_{50}$ μm |
|---|---|---|---|
| | 1 hr | 24 hr | |
| Glutamine | 10.32 | 50.72 | 13.31 |
| Valine | 14.16 | 71.93 | 12.92 |
| Myoinositol | 47.06 | 56.12 | 31.24 |
| Glycine | 33.93 | 64.68 | 43.98 |
| Alanine | 67.00 | 86.73 | 4.92 |

Release Profile and Particle Size Varies Significantly Depending on the Carrier Used.

Decreasing CaCl$_2$ or NaH$_2$PO$_4$ concentration was found to change the rate of protein release and particle size. In most cases, decreasing either of these resulted in faster release of protein and a decrease in particle size as shown in Table 2. Hence it is possible to tailor the release profile and particle size of formulations based on a specific carrier by varying such parameters.

TABLE 2

The effect of varying NaH$_2$PO$_4$ and CaCl$_2$ concentration on the protein release profile and particle sizes of Cap modified BSA/Gln PCMC Formulations

| CONCENTRATION | | PROTEIN RELEASED (%) at | | SYMPATEC X$_{50}$ μm |
|---|---|---|---|---|
| NaH$_2$PO$_4$ (mM) | CaCl$_2$(mM) | 1 hr | 24 hr | |
| 50 | 10 | 10.32 | 50.72 | 13.31 |
| 50 | 5 | 75.22 | 90.76 | 6.37 |
| 25 | 10 | 52.85 | 80.30 | 9.02 |

Slow release CaP modified PCMC could also be prepared at higher pH using disodium hydrogen phosphate buffer (Na$_2$HPO4, pH ~8) and treating these with CaCl$_2$ in the same 2-step procedure. The release characteristics of these samples are shown in Table 3.

TABLE 3

Slow Release CaP modified BSA PCMC Formulations prepared from various carriers using 25 mM Na$_2$HPO$_4$ (pH ~8) and 5 mM CaCl$_2$

| CARRIER | PROTEIN RELEASED (%) at | | SYMPATEC X$_{50}$ μm |
|---|---|---|---|
| | 1 hr | 24 hr | |
| Glutamine | 38.82 | 63.67 | 11.82 |
| Valine | 62.62 | 72.62 | 6.01 |
| Myoinositol | 69.43 | 76.86 | 11.58 |
| Glycine | 65.31 | 73.73 | 13.96 |

For each of the carriers the effect of increasing Na$_2$HPO$_4$ or CaCl$_2$ concentration on the protein released was studied. In all cases, increasing the level of phosphate had a limited effect. In contrast, when the concentration of CaCl$_2$ was increased, protein was released more slowly from the particles. Generally this was also accompanied by an increase in particle size. Hence, by varying the concentration of $CaCl_2$, it is possible to tailor the release profile and particle size of formulations based on $Na_2HPO_4$. These effects are shown in Table 4 for CaP modified BSA/Val PCMCs.

TABLE 4

The effect of varying $Na_2HPO_4$ and $CaCl_2$ concentration on the protein release profile and particle sizes of CaP modified BSA/Val PCMC Formulations

| CONCENTRATION | | PROTEIN RELEASED (%) at | | |
|---|---|---|---|---|
| $Na_2HPO_4$ (mM) | $CaCl_2$(mM) | 1 hr | 24 hr | SYMPATEC $X_{50}$ μm |
| 25 | 5 | 62.6 | 72.6 | 6.01 |
| 50 | 5 | 52.99 | 72.7 | 5.87 |
| 25 | 10 | 19.61 | 59.39 | 17.27 | that the level of soluble calcium ions present in the final powder can be minimised—the presence of soluble calcium ions may adversely affect live cells targeted for treatment with the particles. Bovine serum albumin was used as an illustrative example in these experiments however comparable results may be obtained by substituting in the target bioactive molecule or molecules of choice in place of BSA at similar or lower concentrations.

In Process A a phosphate containing aqueous coprecipitation stream was combined directly with a stream of miscible organic solvent containing $CaCl_2$ using a static mixture. The resultant suspension was then further agitated for up to 1 hour to complete the formation of the calcium phosphate layer.

In Process B, a continuous method for making soluble phosphate-containing PCMC was applied firstly by combining pumped streams of aqueous coprecipitation mixture and miscible organic solvent using a static mixer. To prepare sustained release particles the output of this mixing process was then combined with a third pumped stream of $CaCl_2$ dissolved in organic solvent using a second static mixer. The resultant suspension was then further agitated for up to 1 hour to complete the formation of the calcium phosphate layer.

Many different types of pumps and mixers could be used to continuously combine the different aqueous and solvent streams. In this example we have used readily available commercial equipment but one skilled in the art will recognise it is possible to apply the process with a range of different equipment.

Conclusion

These data show it is possible to vary the particle size and rate of protein release from CaP modified PCMC. Formulations of therapeutic molecules or vaccines can therefore be tuned to provide the required potency or dose regime. The technology can be applied at both low and high pH and so can be applied to biomolecules with different pH stability profiles.

Example 2

Production of Calcium Phosphate Sustained-Release PCMC by a Continuous Manufacturing Process Sustained release PCMC can be advantageously manufactured using a continuous production process scalable for commercial applications. Two different approaches are demonstrated for preparing calcium phosphate treated particles. Both of these approaches provide the calcium chloride dissolved in an organic solvent—this enables variable excesses of this component to be used without adversely affecting the size and shape of the particles—thus during manufacture it is possible to tune different aspects of the particle properties such as the size and release profiles independently from each other. Furthermore, the excess calcium chloride may be easily removed in the solvent when the particles are isolated such Detailed Methodology Equipment for Process A and B Pumps used were Watson Marlow peristaltic types: Model 520U with 6.4 mm Marprene element for the organic solvent stream and 520Du with 3.2 mm Marprene element for aqueous and $CaCl_2$ solution streams. These pumps were used to pump material from the aqueous and organic reservoirs into the static mixers. The 3.1 mm i.d. static mixers were 4-point cross-shaped and made from polypropylene (Kartell). Tubing used was Watson Marlow Silicone tubing except for Marprene tubing at manometer inlet and outlet. The static mixer inlets were placed inside the tubing and secured with cable ties. The aqueous solution was provided in a 100 ml burette connected to the pump via a short length of tubing. Between the primary static mixer and aqueous line there was a non-return valve (Kartell) to prevent organic solvent from entering. To monitor pressure within the system a manometer was vertically held on a clamp stand with an inlet at top and outlet at bottom. Organic solvent and solutions of $CaCl_2$ in organic solvent were held in a conical flask or Duran bottle. Post precipitation agitation was applied to the suspension using a Heidolph Paddle impeller (straight blade stainless steel, Blade size: 50×12 mm stainless steel, rod diameter 8 mm, length 400 mm) which was set at ~0.5 cm from the inside base of the 10.5 cm diameter vessel to minimize settling, close to the fluid centre. Removal of the PCMC from suspension was carried out using a Whatman vacuum filter unit using 101 mm diameter, 0.45 μm pore size, Millipore Durapore filter paper. For aseptic processing the aqueous and solvent streams may be supplied in sterile reservoirs and pumped through tubing and mixers that has been autoclaved Running Process A The entire continuous system was first rinsed with deionised water, and then the organic solvent line was primed with ~200 ml solvent. The aqueous line was filled up to the first non-return valve. The aqueous and the solvent stream containing $CaCl_2$ were pumped from the burette and Duran respectively into the cross mixer using the peristaltic pumps. The aqueous stream was pumped at 50 ml/min and the organic solvent stream at 950 ml/min. A 2-prong forked component was used to split the organic solvent stream so that it entered the 4 point cross mixer from two opposing directions perpendicular to the input aqueous flow and output product flow. The first 500 ml produced was discarded to ensure system equilibration and the resultant suspension (typically ~500 ml) was collected and agitated using the impeller, typically for 1 h at 400 rpm. Particles were isolated from the suspension by filtration of 200 ml aliquots on a membrane filter and air dried.

Running Process B

The entire continuous system was first rinsed with deionised water, and then the organic solvent line was primed with solvent and the third line with solvent containing $CaCl_2$. The aqueous line was filled up to the first non-return valve. The aqueous and precipitation solvent were pumped from the burette and Duran respectively into the first cross mixer using the peristaltic pumps. The aqueous stream was pumped at 50 ml/min, the organic solvent stream at 830 ml/min. A 2-prong forked component was used to split the organic solvent stream so that it entered the 4 point cross mixer from two opposing directions perpendicular to the input aqueous flow and output product flow. The $CaCl_2$ organic solvent solution stream was pumped at 120 ml/min from the Duran and combined in a similar way using a second static cross mixer, attached to 1 m of inter-mixer tubing exiting from the first mixer. The end-tube (after the $2^{nd}$ mixer) was 1 m long with 3.2 mm i.d. To make the setups comparable the Process A end tube was equal in length (2 m) to the sum of the Process B inter-mixer tube and end tube. The lengths of tubing may be varied. The first 500 ml produced was discarded to ensure system equilibration and the resultant suspension (typically ~500 ml) was collected and agitated using the impeller, typically for 1 h at 400 rpm. Particles were isolated from the suspension by filtration 200 ml aliquots on a membrane filter and air dried.

Analysis of Samples

Each powder was analysed to measure kinetics of protein release in PBS buffer. Measurements were carried out in duplicate at ≥3 time points typically over 96 h. On re-suspension in PBS buffer all samples were kept on a blood rotator at 25 rpm and 22° C. ambient temperature.

Compositions Used for Sample Preparation

Sustained Release BSA/L-glutamine PCMC (Process A)

An aqueous stream containing L-Glutamine (20 mg/ml), $Na_2HPO_4$ (3.55 mg/ml) and BSA (4 mg/ml) was mixed with an isopropanol stream containing $CaCl_2$ (0.58 mg/ml) and following agitation for 1 hour the particles were isolated and the protein release measured. Sample identifier=CaP_Gln_ContA Sustained Release BSA/L-Glutamine PCMC (Process B)

An aqueous stream containing L-Glutamine (20 mg/ml), $Na_2HPO_4$ (3.55 mg/ml) and BSA (4 mg/ml) was mixed with an isopropanol stream and the resultant output mixture further mixed with a stream of isopropanol containing $CaCl_2$ (4.6 mg/ml). Following agitation for 1 hour the particles were isolated and the protein release measured. Sample identifier=CaP_Gln_ContB Preparation of Sustained Release BSA/L-Glycine PCMC (Process A)

An aqueous stream containing glycine (100 mg/ml), $Na_2HPO_4$ (14.2 mg/ml) and BSA (20 mg/ml) was mixed with an isopropanol stream containing $CaCl_2$ (2.32 mg/ml) and following agitation for 1 hour the particles were isolated and the protein release measured. Sample identifier=CaP_Gly_ContA Preparation of Sustained Release BSA/L-Glutamine PCMC (Process B)

An aqueous stream containing glycine (100 mg/ml), $Na_2HPO_4$ (3.55 mg/ml) and BSA (20 mg/ml) was mixed with an isopropanol stream and the resultant output mixture further mixed with a stream of isopropanol containing $CaCl_2$ (18.4 mg/ml). Following agitation for 1 hour the particles were isolated and the protein release measured. Sample identifier=CaP_Gly_ContB Results

TABLE

Release of BSA on suspension in PBS.

| Time (h) | CaP_Gln_ContA Cumulative release (%) | CaP_Gln_ContB Cumulative release (%) |
|---|---|---|
| 4 | 37.6 | 42.9 |
| 24 | 64.5 | 67.0 |
| 96 | 74.8 | 76.4 |

TABLE

Release of BSA on suspension in PBS.

| Time (h) | *CaP_Gly_ContA Cumulative release (%) | *CaP_Gly_ContB Cumulative release (%) |
|---|---|---|
| 0 | 14.4 | 28.2 |
| 3 | 23.4 | 25.8 |
| 19 | 50.6 | 53.1 |
| 26 | 56.9 | 59.0 |
| 43 | 59.6 | 61.4 |
| 50 | 60.9 | 62.3 |
| 67 | 63.0 | 64.9 |
| 73 | 63.6 | 64.5 |
| 139 | 66.3 | 66.5 |

*Circular dichroism spectroscopy was used to demonstrate that protein released gave a near identical spectrum to the stock solution and therefore retained a native conformation.

These data demonstrate that sustained release PCMC can be prepared using a continuous manufacturing process. This is an efficient and scalable process well suited to commercial manufacture.

Example 3

Sustained Release Particles Containing ODN-CpG Adjuvants

In order to improve the potency of vaccines it is known that it can be advantageous to include adjuvants. In this example we demonstrate inclusion of immunostimulatory oligodeoxynucleotides (ODN) that contain cytosine-guanine (CpG) motifs into sustained release particles. ODN-CpG are powerful stimulators of innate as well as adaptive immune responses and exert their activity through triggering of Tolllike receptors. Extending the release of CpG will increase the potency of vaccine particles. In this example we have included the CpG, TCCATGACGTTCCTGAATAAT and prepared sustained release samples by applying a calcium phosphate coating with and without a model antigen, bovine serum albumin (BSA).

Those skilled in the art will appreciate that a wide range of vaccine particles may be prepared by substituting the BSA and/or CpG with a similar aqueous concentration of other target antigens or adjuvants, including proteins, peptides, polysaccharides, plasmids, DNA, RNA, virus particles, virus-like particles, attenuated virus particles, toxoids, allergans, toll receptor binders and mixtures and conjugates thereof and then applying the calcium phosphate coating in a similar way.

Particle Preparation

CaPPatCpG1_8_001 Insoluble

An aqueous mixture was prepared using 192 µl of BSA stock solution (1.6 mg/ml) and 113 µl of CPG stock solution (10 mg/ml) gently mixed with 3.0 ml of glutamine (25 mg/ml) dissolved in 25 mM $NaH_2PO_4$, 25 mM NaCl. 3 ml of this mixture was added dropwise using a 1 ml pipette into 52.5 ml of dry Pr2OH, while mixing with a magnetic stirring bar (750 rpm) and left to stir for a further minute. To this was added 7.5 ml $CaCl_2$ in Pr2OH (6.2 mg/ml) added in one lot using a 10 ml pipette and the suspension was mixed for 2 min. The magnetic stirring bar was removed and the bottle transferred to a Vibrax orbital shaker (speed 800) for 1 hour. The particles were then filtered and dried overnight in air. The loading of the antigen, BSA, in these particles is c.a. 0.3% w/w and the loading of the adjuvant, CpG, is c.a. 1.2% w/w CaPPatCpG1_8_002 Insoluble An aqueous mixture was prepared using 192 µl of BSA stock solution (1.6 mg/ml) and 113 µl of CPG stock solution (10 mg/ml) gently mixed with 3.0 ml of glutamine (25 mg/ml) dissolved in 50 mM $NaH_2PO_4$, 25 mM NaCl. 3 ml of this mixture was added dropwise using a 1 ml pipette into 52.5 ml of dry Pr2OH, while mixing with a magnetic stirring bar (750 rpm) and left to stir for a further minute. To this was added 7.5 ml $CaCl_2$ in Pr2OH (12.32 mg/ml) added in one lot using a 10 ml pipette and the suspension was mixed for 2 min. The magnetic stirring bar was removed and the bottle transferred to a Vibrax orbital shaker (speed 800) for 1 hour. The particles were then filtered and dried overnight in air.

CaPPatCpG1_8_005 Insoluble

An aqueous mixture was prepared using 113 µl of CPG stock solution (10 mg/ml) gently mixed with 3.0 ml of glutamine (25 mg/ml) dissolved in 25 mM $NaH_2PO_4$, 25 mM NaCl. 3 ml of this mixture was added dropwise using a 1 ml pipette into 52.5 ml of dry Pr2OH, while mixing with a magnetic stirring bar (750 rpm) and left to stir for a further minute. To this was added 7.5 ml $CaCl_2$ in Pr2OH (6.2 mg/ml) added in one lot using a 10 ml pipette and the suspension was mixed for 2 min. The magnetic stirring bar was removed and the bottle transferred to a Vibrax orbital shaker (speed 800) for 1 hour. The particles were then filtered and dried overnight in air.

CaPPatCpG1_8_006 Insoluble

An aqueous mixture was prepared using 113 µl of CPG stock solution (10 mg/ml) gently mixed with 3.0 ml of glutamine (25 mg/ml) dissolved in 50 mM $NaH_2PO_4$, 25 mM NaCl. 3 ml of this mixture was added dropwise using a 1 ml pipette into 52.5 ml of dry Pr2OH, while mixing with a magnetic stirring bar (750 rpm) and left to stir for a further minute. To this was added 7.5 ml $CaCl_2$ in Pr2OH (12.32 mg/ml) added in one lot using a 10 ml pipette and the suspension was mixed for 2 min. The magnetic stirring bar was removed and the bottle transferred to a Vibrax orbital shaker (speed 800) for 1 hour. The particles were then filtered and dried overnight in air.

Determination of the Total Amount of Oligo in CaP Sample

In order to determine the total amount of oligo bound within CaP treated particles a method is required to fully dissolve the sustained release samples. This method uses non-physiological conditions based on dissolution within a tris/citrate/EDTA buffer. Dry CaP-treated PCMC powders containing ~2 mg of antigen or adjuvant (assuming 100% yield) were weighed into a 7 ml vial and 2 ml of a mixture containing Tris-HCl buffer (20 mM, pH 7.4), sodium citrate (50 mM), EDTA (1 mM) was added. The mixture was stirred for 10 min until a clear solution was obtained and then transferred to a cuvette for UV determination of CpG concentration. Solutions that still exhibited scattering after 10 mins were diluted by a factor of two and/or treated with additional EDTA to complete dissolution.

Measurement of Release Profiles for CpG and BSA 20 mg samples were suspended in PBS and agitated on a blood rotator at 25 rpm and 22° C. ambient temperature. Aliquots were removed at various time intervals from centrifuged suspension. The concentration of released CpG was determined by UV absorbance at 280 nm using RP-HPLC. The concentration of released BSA was determined using a BioRad protein microassay.

Results

TABLE

Release of total amount of ODN from CaP treated particles by dissolution in Tris/Citrate/EDTA buffer at concentration of 6.8 mg/ml of powder.

| Sample ID | Formulation | Nett Oligo Release (%) |
|---|---|---|
| CaPPatCpG1-8-001 | BSA/CpG/Gln (25 mM $NaH_2PO_4$, 5 mM $CaCl_2$) medium mixing | 96.573 |
| CaPPatCpG1-8-002 | BSA/CpG/Gln (50 mM $NaH_2PO_4$, 10 mM $CaCl_2$) medium mixing | 98.014 |
| CaPPatCpG1-8-005 | CpG/Gln (25 mM $NaH_2PO_4$, 5 mM $CaCl_2$) medium mixing | 99.522 |
| CaPPatCpG1-8-006 | CpG/Gln (50 mM $NaH_2PO_4$, 10 mM $CaCl_2$) medium mixing | 98.090 |

These data show that inclusion of the CpG into the particles is a very efficient process with greater than 95% of the ODN being included within each of the formulations. This is particularly advantageous because the loading of adjuvant within the particles can be straightforwardly tuned for optimum potency and the manufacturing process will be cost-effective.

TABLE

| | Time 0 | Time 24 hr | |
|---|---|---|---|
| Sample ID | CpG released (%) | CpG released (%) | BSA released (%) |
| CaPPatCpG1-8-001 | 27.7 | 33.7 | 42.8 |
| CaPPatCpG1-8-002 | 4.2 | 7.1 | 9.4 |
| CaPPatCpG1-8-005 | 24.2 | 31.8 | — |
| CaPPatCpG1-8-006 | 19.0 | 34.5 | — |

CaP treated particle suspended in PBS at particle concentration of 20 mg/ml of powder.

These data demonstrate that it is possible to prepare CaP treated particles in which the release of the ODN-CpG is significantly delayed relative to fully soluble particles. In addition sustained release particles containing both an antigen and an adjuvant can be prepared with the release profile of each being tuneable to be faster (CaPPatCpG1-8-001) or slower CaPPatCpG1-8-002. This is advantageous because it means the vaccines can be easily altered in order to optimise the type and intensity of the immune response. In experiments with sustained release particles of a proprietary antigen prepared by a similar process a strong cell-mediated immune response was observed. Soluble particles containing the antigen but no adjuvant were not immunogenic.

As can be seen, advantageously the sustained release particles can be prepared from water soluble bioactive coated microcrystals without comprising any synthetic or natural polymers. By polymers it is meant molecules that exhibit a range of molecular weights that are formed by polymerisation of one or more monomers and which make up part of the particle matrix but are not the bioactive molecule that is being released. Such polymers often require to be included in sustained release particles because they impart specific desirable physical properties such as low aqueous solubility, biodegradability or because they are surface active. Except for the therapeutically active molecules contained therein the particles of the invention are preferably comprised solely of non-polymeric compounds with a molecular weight of less than 1000 Da or preferably 500 Da such as amino acids and metal salts. They may thus be easily cleared on dissolution following administration to living organisms and do not require degradation or clearance of a polymer to take place."

providing an organic solution comprising a precipitated water-soluble inorganic first metal salt, one or more precipitated bioactive molecules, a precipitated material capable of forming said microcrystals, and a dissolved second metal salt, carrying out a double decomposition reaction in said organic solution between the water soluble inorganic first metal salt and the dissolved second metal salt to form bioactive molecule coated microcrystals comprising a coating of a third metal salt, and wherein the third metal salt, formed by the double decomposition reaction, is present on the surface of the microcrystals, and wherein the microcrystals are water soluble/aqueous solution-soluble microcrystals.

2. The method according to claim 1 wherein the metal salt which is coated on the surface of the microcrystals is a metal phosphate, metal carbonate or metal hydroxide.

3. The method according to claim 2 wherein the second metal salt is calcium phosphate, calcium pyrophosphate, aluminum hydroxide, aluminum phosphate, calcium carbonate, iron hydroxide, magnesium phosphate, magnesium carbonate, zinc phosphate or combinations thereof.

4. The method according to claim 1 wherein the first metal salt is selected from $Na_2HPO_4$, $NaH_2PO_4$, $K_2HPO_4$, or $KH_2PO_4$ and the second metal salt is $CaCl_2$.

5. The method according to claim 1 wherein the method is conducted as a continuous process.

6. The method according to claim 5 wherein the delay in dissolution of the bioactive molecule is up to 240 hours.

7. The method according to claim 1 wherein the prolonged release is up to 48 hours.

8. A method of preparing bioactive molecule coated microcrystals, which crystals display a delayed and/or prolonged release profile in water and/or aqueous solution, comprising the steps of:
  (a) providing an aqueous solution comprising coprecipitant molecules and bioactive molecules, wherein the aqueous solution further comprises a source of a first metal salt;
  (b) providing a water-miscible organic solvent or a solvent solution comprising a water miscible organic solvent;

The invention claimed is:

1. A method of preparing bioactive molecule coated microcrystals which display a delayed and/or prolonged release profile of said bioactive molecule in water and/or aqueous solution, comprising the steps of:

(c) mixing said aqueous solution with said solvent solution such that coprecipitation of the coprecipitant and the bioactive molecules is initiated, resulting in formation of a suspension of aqueous soluble microcrystals comprising bioactive molecules and the first salt coated on a coprecipitant comprising core; and (d) contacting a water miscible organic solvent comprising a solution of a second salt or a metal complex containing a polyvalent metal cation with the suspension comprising microcrystals obtained in step (c) so as to form a coating of a water-insoluble third salt on the surface of the microcrystals, formed from the double decomposition of said first and second salts or complexes, wherein the microcrystals are bioactive molecule-coated, water soluble/aqueous solution-soluble microcrystals, the first metal salt is aqueous soluble and contains a polyvalent cation and the second metal salt is soluble in a water-miscible organic solvent, and the third salt is a metal salt that is water-insoluble, sparingly soluble or poorly water-soluble.

9. The method according to claim 8 wherein the metal salt which is coated on the surface of the microcrystals is a metal phosphate, metal carbonate or metal hydroxide.

10. The method according to claim 9 wherein the metal salt is calcium phosphate, calcium pyrophosphate, aluminum hydroxide, aluminum phosphate, calcium carbonate, iron hydroxide, magnesium phosphate, magnesium carbonate, zinc phosphate or combinations thereof.

11. The method according to claim 8 wherein the first metal salt is selected from $Na_2HPO_4$, $NaH_2PO_4$, $K_2HPO_4$, or $KH_2PO_4$ and the second metal salt is $CaCl_2$.

12. The method according to claim 8 wherein the method is conducted as a continuous or batch process.

13. The method according to claim 8 wherein the delay in dissolution of the bioactive molecule is up to 240 hours.

14. The method according to claim 8 wherein the prolonged release is up to 48 hours.

15. The method of claim 8, wherein the organic solvent used in the precipitation in step (c) and the coating in step (d) comprises the same solvent.

16. The method of claim 1, wherein the microcrystals comprise one or more agents selected from the group consisting of proteins, peptides, polysaccharides, plasmids, DNA, RNA, virus particles, attenuated virus particles, toxoids, allergans, toll receptor binders, conjugates thereof, and mixtures thereof.

17. The method of claim 8, wherein the microcrystals comprise one or more agents selected from the group consisting of proteins, peptides, polysaccharides, plasmids, DNA, RNA, virus particles, attenuated virus particles, toxoids, allergans, toll receptor binders, conjugates thereof, and mixtures thereof.

18. The method of claim 1, wherein the bioactive molecules are selected from the group consisting of therapeutic proteins, therapeutic peptides, antibodies, antibody fragments, hormones, synthetic DNA, natural DNA, enzymes, polysaccharides, and combinations thereof.

19. The method of claim 8, wherein the bioactive molecules are selected from the group consisting of therapeutic proteins, therapeutic peptides, antibodies, antibody fragments, hormones, synthetic DNA, natural DNA, enzymes, polysaccharides, and combinations thereof.

20. The method of claim 1, further comprising drying the bioactive molecule coated microcrystals.

21. The method of claim 8, further comprising drying the bioactive molecule coated microcrystals.

* * * * *